US008315899B2

(12) United States Patent
Samuhel et al.

(10) Patent No.: US 8,315,899 B2
(45) Date of Patent: Nov. 20, 2012

(54) METHOD OF SCHEDULING (75) Inventors: Frank Samuhel, Dromana (AU); Stuart Lucas, Murrumbeena (AU); Christopher Bowen, Burwood (AU)

(73) Assignee: Leica Biosystems Melbourne Pty Ltd, Victoria (AU)

( * ) Notice: Subject to any disclaimer, the term of this patent is extended or adjusted under 35 U.S.C. 154(b) by 1242 days.

(21) Appl. No.: 10/546,772

(22) PCT Filed: Feb. 24, 2004

(86) PCT No.: PCT/AU2004/000229
§ 371 (c)(1),
(2), (4) Date: Oct. 27, 2006

(87) PCT Pub. No.: WO2004/074847
PCT Pub. Date: Sep. 2, 2004

(65) Prior Publication Data
US 2007/0038491 A1 Feb. 15, 2007

(30) Foreign Application Priority Data
Feb. 24, 2003 (AU) ............................... 2003900810

(51) Int. Cl.
*G06F 15/02* (2006.01)

(52) U.S. Cl. ..................................................... 705/7.12

(58) Field of Classification Search .................. 705/8, 9, 705/7.12, 7.13
See application file for complete search history.

(56) References Cited

U.S. PATENT DOCUMENTS

| 4,058,367 | A | | 11/1977 | Gilford | |
|---|---|---|---|---|---|
| 5,282,149 | A | | 1/1994 | Grandone et al. | |
| 5,355,439 | A | * | 10/1994 | Bernstein et al. | 700/247 |
| 5,482,861 | A | * | 1/1996 | Clark et al. | 436/48 |
| 5,573,727 | A | * | 11/1996 | Keefe | 422/63 |
| 5,875,286 | A | | 2/1999 | Bernstein et al. | |
| 6,096,561 | A | * | 8/2000 | Tayi | 436/518 |

FOREIGN PATENT DOCUMENTS

| WO | WO 9322686 | 11/1993 |
|---|---|---|
| WO | WO 9533240 | 12/1995 |
| WO | WO 9845679 A1 | 10/1998 |

OTHER PUBLICATIONS

Rapid, automated assay for progesterone on the Abbott AxSYM (TM) analyzer by David H. Wilson et al. Clinical Chemistry 44:1 86-91 (1998).*
Supplemental European Search Report dated Jan. 14, 2011.

* cited by examiner

*Primary Examiner* — Beth V Boswell
*Assistant Examiner* — Ernest A Jackson
(74) *Attorney, Agent, or Firm* — Sughrue Mion, PLLC (57) ABSTRACT

A method and apparatus for scheduling are disclosed. The apparatus applies tests to microscope slides, where the slides are loaded in trays. Each tray is treated as a batch, and batches may be interleaved to reduce the total running time of testing all slides in up to three batches. The batches of slides have protocols that define the application of reagents such as primary antibodies. The protocols define open times, where no common resources are used, and use times, where common resources are used. The scheduler operates to ensure that the use times between batches does not overlap, without leaving the next step in the protocol for an excessive period of time.

5 Claims, 7 Drawing Sheets

METHOD OF SCHEDULING

FIELD OF THE INVENTION

This invention relates to a method of scheduling particularly, but not exclusively, scheduling of protocols in a biological tissue testing apparatus.

BACKGROUND

A method and apparatus for automated tissue assay is disclosed in U.S. Pat. No. 5,355,439. The apparatus operates by determining particular tests to be applied to a plurality of samples. Each test comprises a number of distinct steps, with respective starting times and completion times. The apparatus schedules the steps of multiple tests into a single time sequence by interleaving the steps of different tests. Time conflicts that result from interleaving the various starting and completion times are resolved by adjusting the duration of one or more of the steps.

OBJECT

The present invention seeks to provide an alternative method of scheduling.

SUMMARY OF THE INVENTION

In accordance with one aspect of the present invention there is provided a method of applying tests to a plurality of slides including:
placing the slides in a plurality of trays
placing each tray in a receptacle having slide supports for each slide;
applying reagent to the slides in each tray sequentially.

In one form the method includes ascertaining the protocol to be applied to the slides in each tray and scheduling the trays to minimise processing time.

In accordance with the invention, there is provided a method of scheduling tests for a plurality of sample batches, including:
establishing a protocol for each of the batches, with each protocol having at least one block of dispensing and incubation operations, defining use and free times, respectively; and
creating a schedule that contains interleaved blocks from each of the protocols by time shifting the blocks such that use time violations between the blocks are avoided.

Preferably, an initial open time is provided for each block, the open time representing a maximum period within which a first operation of the block needs to commence.

Preferably, a scheduling operation avoids a use time violation between blocks whereby a block of a second batch is delayed until there is no use time violation with the first block of a first batch, and subsequent blocks of each batch are compared for further use time violations; and whereby further use time violations are overcome by delaying one of the blocks until there is no violation; wherein the process is continued until all blocks within all batches are scheduled without use time violations.

Preferably the open times between consecutive blocks are reviewed during the aforementioned scheduling operation to ensure that the time between blocks within any batch does not exceed the maximum open time, thereby avoiding an open time violation.

Preferably, an open time violation is attempted to be resolved by assigning a priority to an offending block of a later batch and swapping that block with an adjacent block of an earlier batch. If an open time violation exists after swapping, the assigned priority is increased so that the start time of the offending block of the second batch is scheduled preferentially of a next adjacent earlier block of the first batch, so as to satisfy both open time and use time requirements.

If, however, an open time violation still exists after a predetermined number of priority increases, the priority of the offending block is no longer increased and, instead, the previous block in the later batch is delayed until both open time and use time requirements are satisfied.

Preferably, the method includes establishing a new schedule to accommodate one or more batches, added after commencement of operations of an initial scheduling.

Alternatively, in the event a new schedule cannot be generated, to accommodate a batch added after commencement of operations of an initial scheduling, one or more hydration steps may be included to extend a start time of the added batch.

Preferably, the dispensing and incubation operations are of a fixed duration. More preferably, reagents applied to the samples of each batch are supplied with a predetermined concentration such that the incubation operations are of the same duration.

Preferably the use time violations are resolved first, then open time violations.

BRIEF DESCRIPTION OF THE DRAWINGS

The invention is described, by way of non-limiting example only, with reference to the accompanying drawings, in which.

DETAILED DESCRIPTION

1. Analysis System

Figure 1:
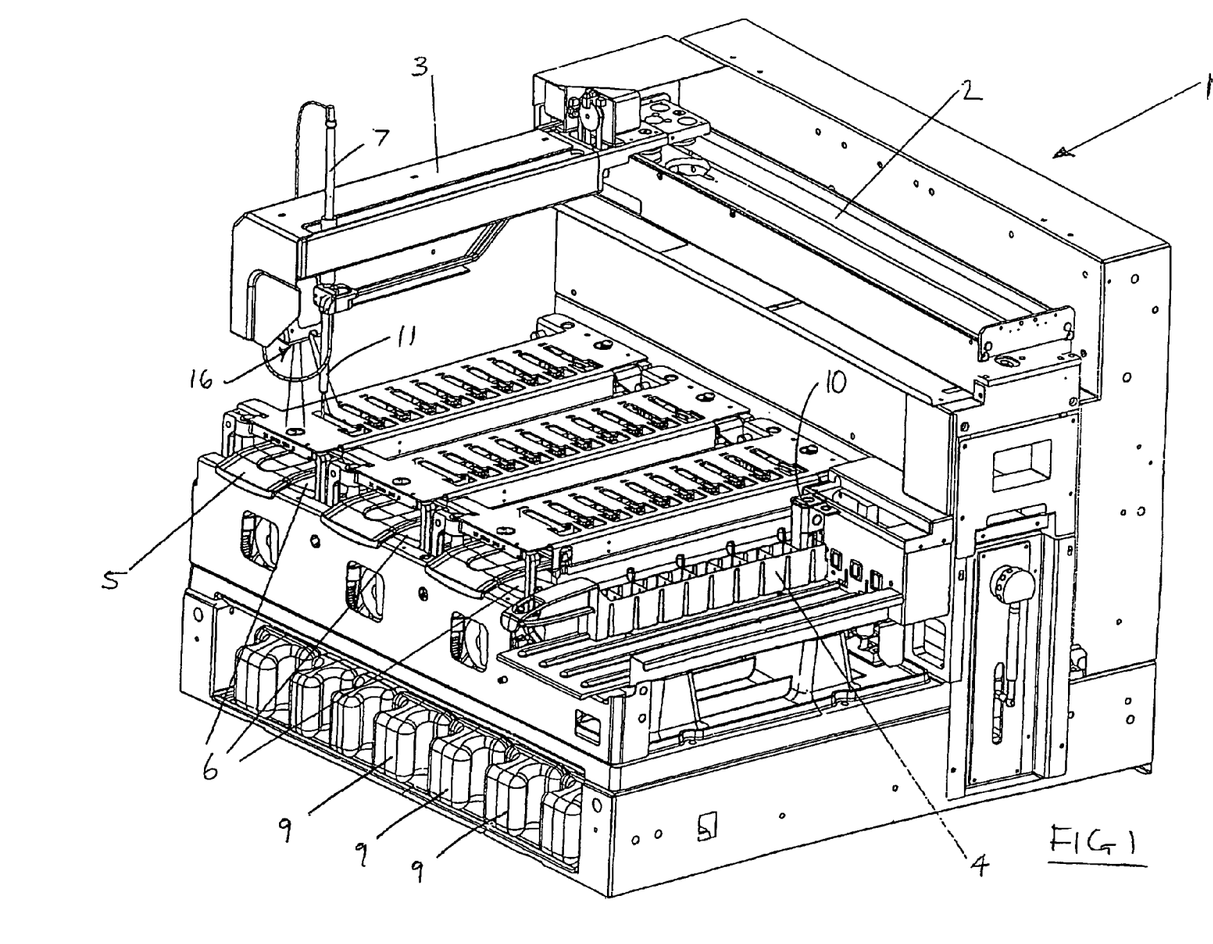
FIG. 1 is a perspective view of a test system.

An analysis system 1, which utilises a scheduling method of the invention, is shown in FIG. 1 as including a testing apparatus 2 which has a robotic arm 3 for transferring test reagents between a reagent tray 4 and sample trays 5 which are received in associated ports 6 in the apparatus 2.

The reagents are transferred by a pipette device 7 which is located on the robotic arm 3. In order to transfer the various reagents, the device is firstly located above an appropriate reagent container 10 and a nozzle 11 is then lowered into the container 10 to withdraw a predetermined volume of reagent. The robotic arm 3 then moves the pipette device 7 into a location above an associated sample tray 5 so that the reagent can be dispensed, as required. The system 1 also includes bulk reagent containers 9 which contain buffer, water and other fluids used during operation of the apparatus 1.

Figure 2:
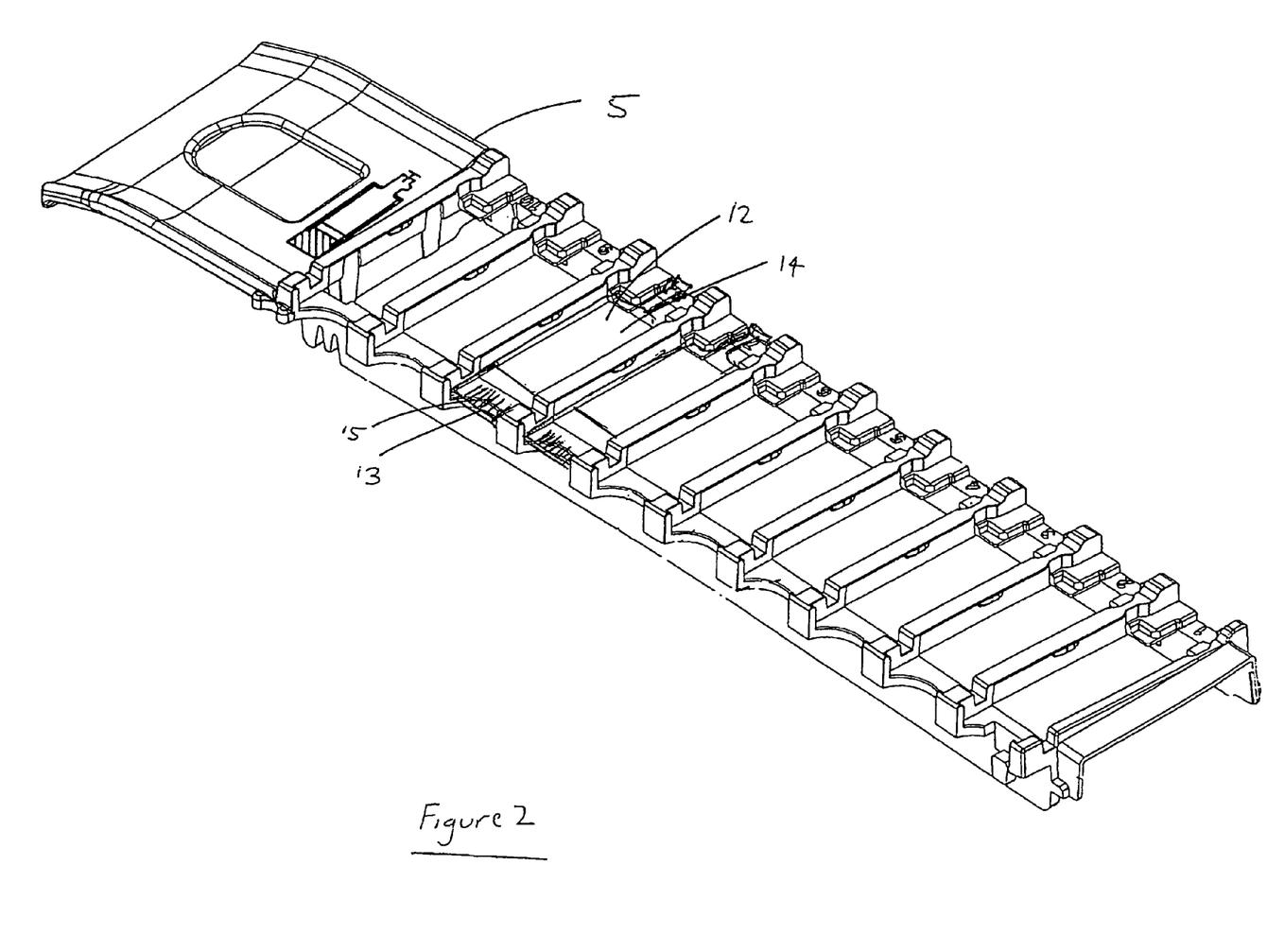
FIG. 2 is a perspective view of a sample tray.
Figure 3:
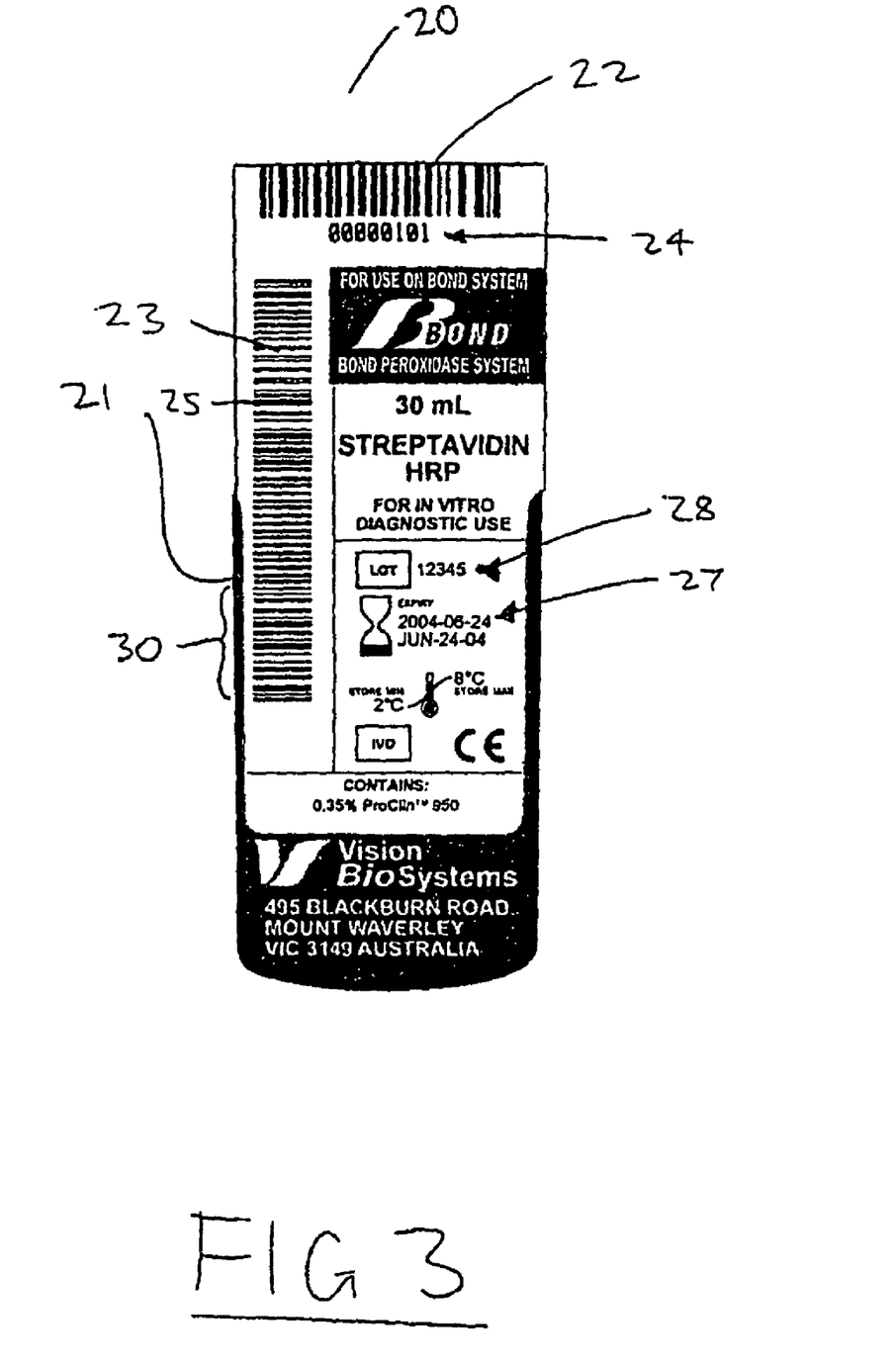
FIG. 3 is a plan view of a tag used on a reagent container.

A suitable identification system is used to ensure correct application of the reagent. For that purpose, each sample is provided on a sample receptacle 12 which is preferably in the form of a sample slide 13, as shown in FIG. 2, with a cover tile 14. The sample slide 13 is provided with a unique identifier 15 which is scanned by a reader 16, which is also carried by the robotic arm 3. The identifier 15 is illustrated as being in the form of a barcode 17 at one end of the slide 13. A similar identifier 20 may be provided on a tag 21 which is shown in FIG. 3 and is adapted to be applied to one of the reagent containers 10.

The tag 21 in fact carries two types of barcode 22,23. The unique identifier 20 which is shown represents an eight-digit number which identifies the actual reagent container 10 itself. An alphanumeric representation 24 of the identifier 20 appears beneath the barcode 22. The second barcode 23 is in the form of a sequence of characters 25 which provide more detailed information relating to the reagent carried within the container 10. The sequence 25 may include thirty characters, which represent data such as product name 26, expiry date 27, lot number 28, serial number, and the like. The sequence 25 also includes embedded identifier code 30 to allow the reagent information to be cross-correlated with the identifier code 20 in the first barcode 22. Again, alphanumeric and pictorial representations of the type of information carried by the sequence of characters is illustrated adjacent the second barcode.

Figure 4:
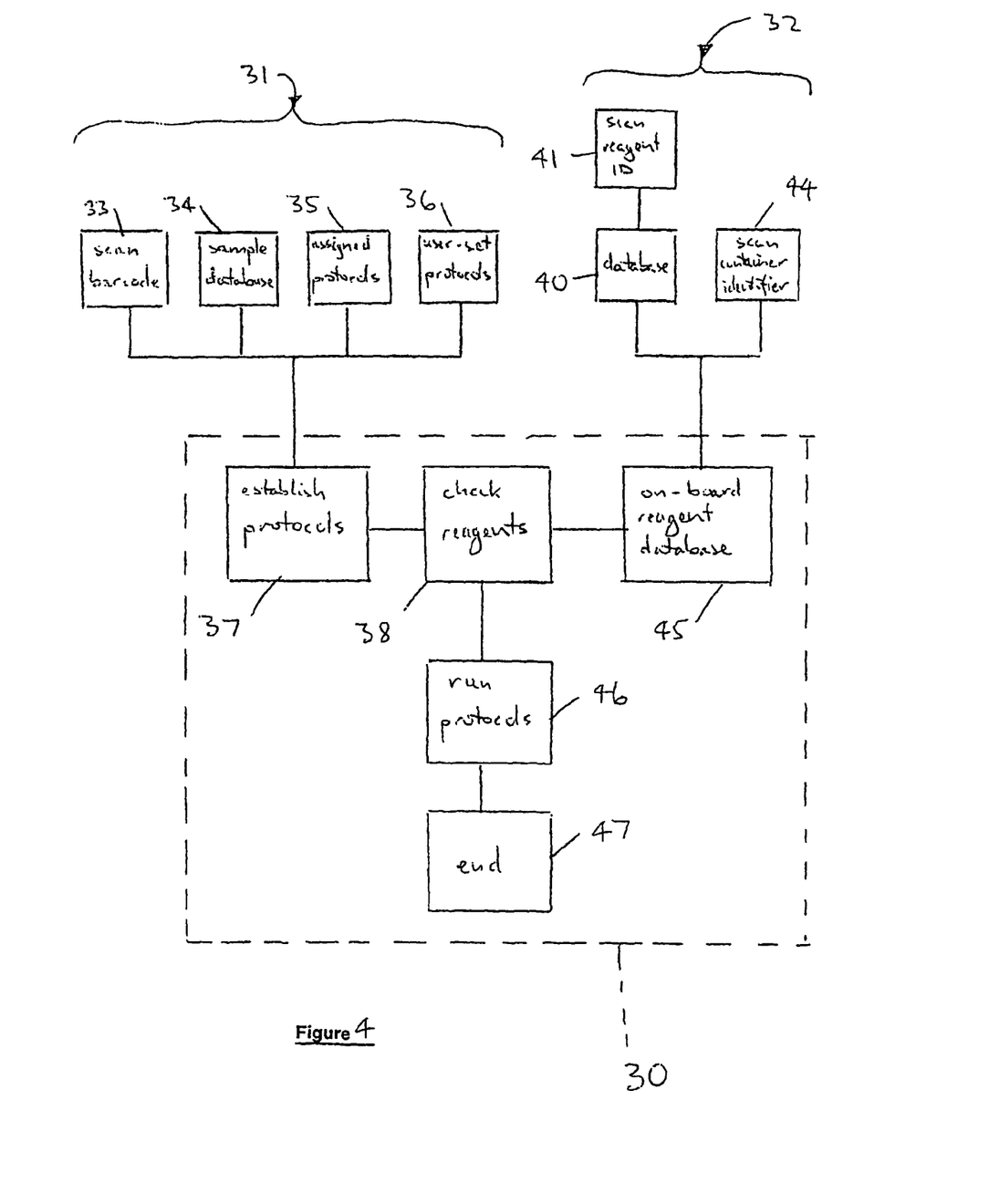
FIG. 4 is a flow chart illustrating use of the system of FIG. 1.

The system 1 also includes a controller 30 which operates the apparatus in a manner indicated by the flow chart illustrated in FIG. 4. In order for a test protocol to be executed, both sample information 31 and reagent information 32 need to be obtained for the purpose of establishing a schedule.

In order to obtain the relevant sample information, a sample tray 5 is firstly inserted in the relevant port 6 of the apparatus and the robotic arm 3 is operated so that the reader 16 can scan each of the identifiers 20 on the relevant slides 13 at step 33. The identifiers 20 are then cross-checked with a sample database at 34 and assigned protocols or user-set protocols are then determined at steps 35 and 36 for each respective slide 13. Once the protocols are established at step 37, a check is conducted at 38 to ensure relevant reagents are present in the apparatus. A suitable alarm may be triggered if additional reagents are required.

In order to establish a reagent database 40, each of the sequence of characters 25 are scanned at step 41 prior to the containers 10 being installed in the reagent trays 4. Such a preliminary scanning step is used to establish a comprehensive database at step 40 of not only those reagents which are on board the apparatus 2 but also those held in, for example, a storage facility (not shown) prior to using the apparatus 2. When a tray 4 is loaded onto the apparatus 2, the robotic arm 3 automatically scans each of the unique identifiers 20 on the containers 10 at 44 and the identifiers 20 are cross-correlated with the database to establish an on-board reagent database at step 45, which allows the controller 30 to determine whether sufficient reagents are present to satisfy the protocols which have been established for each of the samples. Assuming sufficient reagents are present, the controller 30 causes a schedule to be generated and then activates the apparatus 2 to run the test protocols at 46 until all of the various tests are completed at step 47.

The system 1 provides for a number of advantages as a result of using unique identifiers 15,20 of a limited number of characters. Firstly, the identifier barcodes 16,22 can be enlarged to facilitate easier scanning by the reader. Secondly, use of a unique identifier 15 to identify a sample slide 13 allows flexibility insofar as the test protocols to be applied to the sample may be operator modified, as required. Also, in relation to the reagent information 32, scanning of detailed regent information and establishing a reagent database at step 40, prior to conducting test protocols, can reduce the operation time of the apparatus 2 itself.

The scheduling method is now described in detail with reference to FIGS. 5 to 10.

2. Scheduling Method

The types of protocols are predefined by the system, so during registration it is merely a matter of selecting one from a list. It is possible to create your own protocol and save it to the list for later use.

To get the instrument to process the slides, a slide tray having at least one registered slide is loaded into the instrument. At this point the robot arm having the bar code reader will read the bar code of all the slides in the tray and look up their respective bar code IDs. The bar code ID will correspond to a slide ID, and the slide ID will be associated with primary antibody and protocol information.

This process is done for every different slide in a slide tray (say, slide tray 1). After reviewing all the slides and ascertaining the primary antibodies required and protocol information, the instrument checks to see if it has correct type and sufficient quantity of reagents on board. This being the case a protocol is constructed for the all slides. This is not complicated, as all slides within a tray must have the same (or compatible) protocol. This means that while different primary antibodies may be applied to each sample on a slide, the protocol information will be generally the same. Protocol information includes the sequence of steps, and information on each step including:

Durations of each step

Potential open times for a step

Each step duration has two times, being a use time and an open time:

Use time is time when a shared resource is in use. Typically this means the robotic arm, but can mean other hardware of the Bond instrument.

Free time is time where the duration of a step has not completed, but the shared resource is not in use. Typically this is during incubation of the sample after reagent has been applied.

As an example, if a slide is to have a primary antibody applied to the sample, then the time taken to undertake that step includes moving the robot arm to the correct reagent container, withdrawing the right amount of reagent using the pipette, moving to the slide, dispensing the antibody, and moving to a wash station to wash the pipette. However, the primary antibody must be in contact with the sample for some time before being washed off. Therefore, the step is not finished until the primary antibody is washed off, however the robot arm is not required during the incubation, until the washing step.

Also, a step is not just for a single slide, but for as many slides as are present in the tray when it is loaded. Thus if the tray has 10 slides, all with the same protocol, then all the slides will be processed in a single step. An example would be during dispensation of a primary antibody on each slide. While the protocols must all be compatible, the primary antibodies may be all different. However, the instrument is designed so that different primary antibodies all have the same incubation time, and therefore, apart from being sourced from different reagent containers, and the requirement for pipette washing when changing primary antibodies, the robot arm moves from reagent container to slide, to dispense primary antibody onto each slide in the tray, before waiting for the incubation period to end.

A step may also not necessarily be related to a slide at all. For example, after the run begins, one of the early steps will be the mixing of the DAB, which is done on board by mixing reagent from a reagent bottle with other fluids, to a desired concentration, all done in a separate mixing vessel.

Another time is also known for some steps, called an Open time:

Open Time: the maximum legal time that the next block may be delayed.

Thus a the system will generate a protocol for slide tray 1 comprising a number of blocks, each block having a number of steps, each step having at least a use time. Blocks are separated by open times. An open time is stored as a maximum time, in that it could be any time between its maximum time and zero. The amount of actual open time used in a protocol is not known until after the schedule has been finalized.

Figure 5:
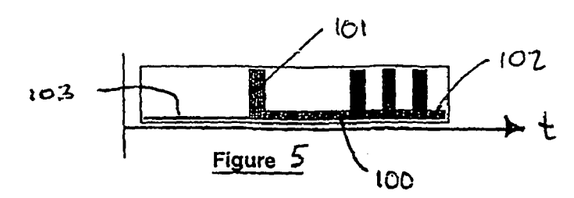
FIG. 5 illustrates a block used for scheduling.

In FIG. 5, the tall rectangles 101 represent use times, the short ones 102 represent free times and the elongate one 103 represents the maximum allowable open time. The horizontal axis 104 is time, and so the width of a rectangle 101,102,103 represents its duration.

Figure 6:
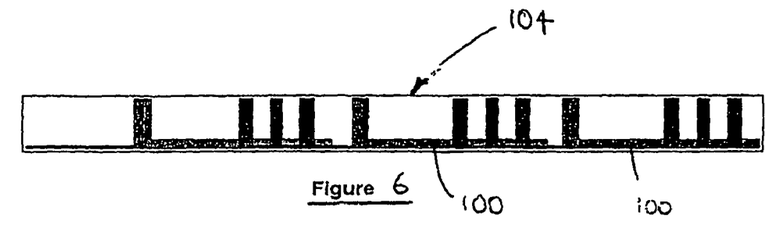
FIG. 6 illustrates a batch, which includes a plurality of blocks.

A protocol 104 (more generally called a batch) consists of one or more of these blocks 100, as illustrated in FIG. 6.

A schedule is built for each slide tray placed into the Bond instrument. Each slide tray may have up to 10 slides. Each slide tray may use a different protocol, however the protocol must be compatible or the same for each slide within a tray. Slides within a tray may also be referred to as a batch, as the method of processing the trays is batch oriented.

After all the trays are entered and the protocols for each tray or batch have been worked out, as above, the scheduler will attempt to interleave the individual schedules for each tray to make an single schedule that minimises the overall run time of the system. Typically this can happen when two or more trays start at the same time, or when a single tray has started, and one or more other trays are loaded into the instrument.

The instrument will have divided each protocol into a number of blocks. Blocks contain at least one step. Each step has at least a use time, and often an open time.

Therefore, after reading in two (for example) trays of slides, the instrument will have two batches stored as schedules, each batch divided into a number of blocks, each block separated by open times. The scheduling program then looks at a first batch and determines the use and free times of each step within the batch. There are several facts to consider: use time violations and open time violations.

Use time violations are where the critical resource is required to be in use by two batches at the same time. This cannot physically occur, as for example, the robot arm cannot be in two places at once and therefore cannot dispense fluid onto two different slides at the same time. The scheduler therefore has to make sure that if blocks overlap, the use times within a block do not overlap.

Figure 7:
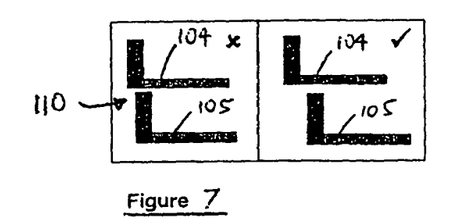
FIG. 7 illustrates use time violations.

In FIG. 7, the schedule 110 on the left shows batches 104,105 which are both trying to use the common resource at the same time. This is a use-time violation. The use times on the right hand side do not overlap, and therefore there is no violation In order to avoid use time violations, blocks 100 in a schedule can be delayed. However, blocks cannot be delayed indefinitely. When a block is delayed too much, this is called an open time violation. An Open time violation occurs when the gap between blocks within the same batch exceeds the maximum time. For example a slide may require application of fluid within a predetermine time (e.g. 10 minutes) to prevent drying of the sample on the slide. If the schedule does not allow for application of fluid within the predetermined period then this is an open time violation. This can result in inconsistent staining or tissue drying out. This too must be avoided.

In FIG. 5, the line or rectangle 103 on the left-hand side represents the open time for the block 100, which is the maximum amount of time that the block can be delayed after the end of the previous block from the same batch 104. This line 103 must overlap with the previous block, or extend to before a start time of the schedule, in order for the block's open time to not be violated.

Figure 8:
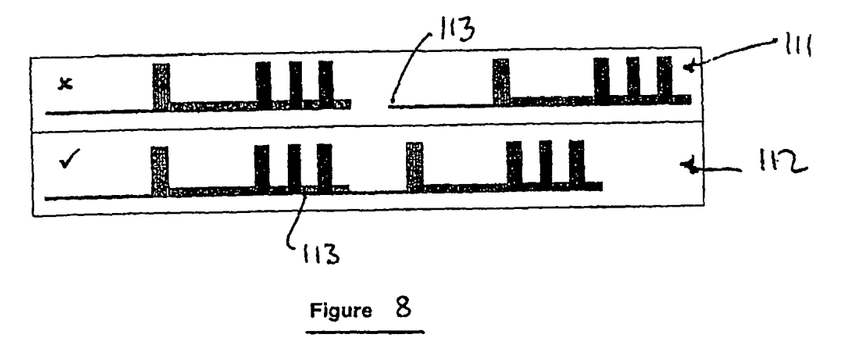
FIG. 8 illustrates open time violations.
Figure 9:
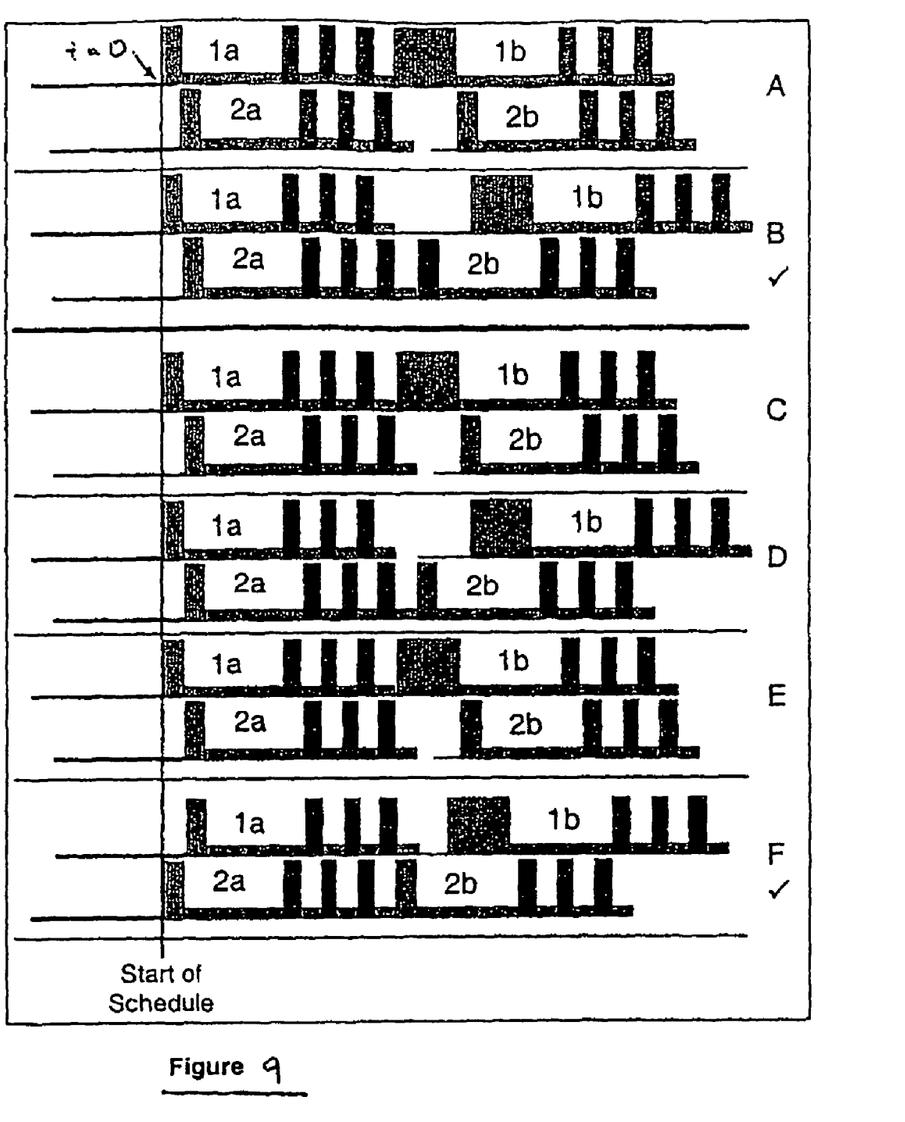
FIG. 9 illustrates open time violation resolution.
Figure 10:
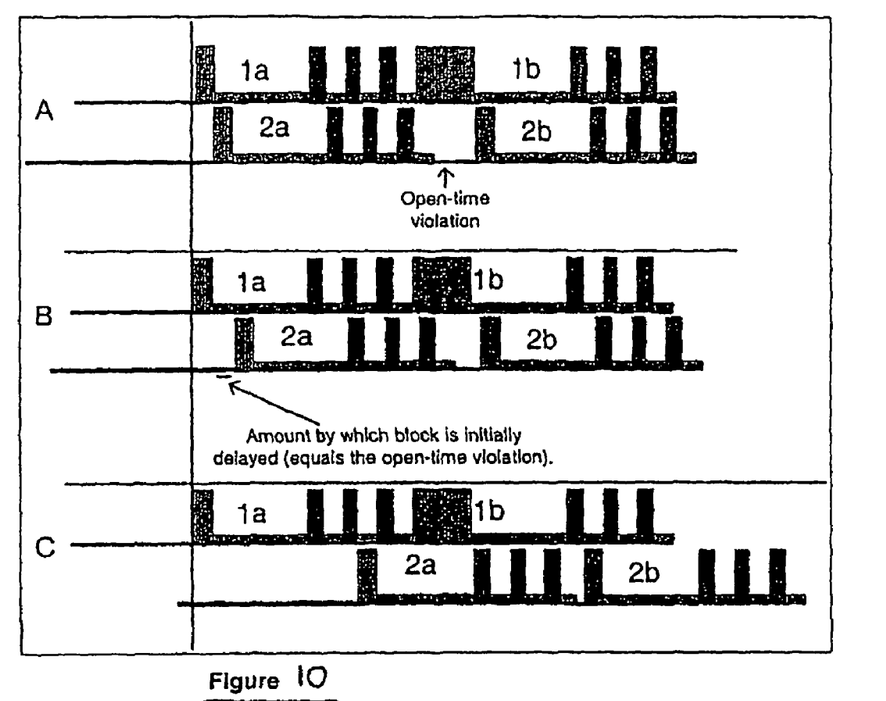
FIG. 10 illustrates use of a catch up parameter.

In FIG. 8, the top section 111 shows a block 100 whose open time is being violated. The bottom section 112 shows a start time 113 of this block 100 adjusted so that its open time is not violated.

Worst case scenario for scheduling would a second batch not starting until the first batch had completed the processing. The best case is where the finishing point of the second batch is not delayed by the first batch. Typically a solution exists between these points and a number of calculations are run to find one or more solutions. Computing power limits the number of tries a computer has to get a solution, and typically more than one solution will be sought from a scheduling run. If more than one successful schedule is achieved, then the schedules are compared and the best schedule selected.

The sequence of dispensation is as follows:

The scheduler is started at a particular time (say time 0). If one or more batches are already being processed, then the blocks currently being processed within those batches will have a start time before time 0. When a new schedule is calculated, any block with a start time before time 0 is non-movable. Other blocks to be scheduled will be placed after these blocks.

Each batch is placed into a separate list, so that, later on, open times can be calculated. (The batches may consist of one tray where processing has already being started, and a new tray, or two newly added trays etc)

The first movable block from each list is pooled into a group. A set of constraints is applied to the group to reduce the list of available blocks. For example, if a batch (batch 1) is running, and two more (batch 2 and 3) are added, then there are three possible blocks that may be scheduled next: the next block from batch 1, or the first block from either batch 2 or 3. Constraints include:

Has the block already been ruled out (see below for definition)
Is the block a master or slave (see below for definition)
Has the blocks start time exceeded the allowable start time?
Has the block already been tried in this position?
What priority is this block?

If more than one block is still available in the group, and they all have the same priority, then a block within the group is selected at random. The selected block is then placed into the schedule based on the completion time of the previous block in the same batch. If the block is the first in a batch then it is scheduled at the end of the non-movable block in front of it.

However, once the first block of each batch has been scheduled, subsequent blocks will be scheduled to start at the completion of the previous block of the same batch. This will overlap with the block already scheduled unless the block already scheduled is the block in the same batch. If the block to be scheduled is in another batch from the previous block then the scheduled block and new block will be scheduled at the same time. A check is made to see of the blocks' use time overlaps, and if so the block to be scheduled is moved by adding time to its start time until the use times no longer overlap.

The added time is then compared to the allowed Open times to determine whether an open time violation has occurred. If an open time violation occurs, the block being scheduled is "unscheduled" and ruled out of selection from the group of available blocks for selection. The scheduling program then looks back to the pool to select another block, and the process begins again.

If all blocks are tried and none can be scheduled, then the scheduler goes back to an earlier scheduled block and unschedules the block, rules it out, then randomly selects another block from the pool of available blocks having the same priority (if there is more than 1). This can keep happening until a workable schedule is found or the number of iterations required to obtain a workable schedule is exceeded, whereupon that attempt at scheduling is stopped, and the whole process restarted.

As the blocks are selected randomly from a pool of available blocks, it is likely that a different block will be selected early on in the process and a new solution space will be produced.

Typically 5 solutions are produced, although this number is arbitrary.

Once the schedules are complete the best schedule of the 5 is selected and used.

The selected schedule is started when the start time of the first scheduled block is reached.

Typically this whole scheduling process takes approximately 30 seconds.

If no successful schedules are derived then an alarm sounds and the user has to wait until the existing schedule has finished.

Has a batch been ruled out: this occurs when a schedule is attempted but the schedule program cannot make a useable schedule in the required number of iterations. It will then go back and deselect the previously scheduled block, ruling it out from selection, so that another block is chosen. This ensures that a number of solution spaces are explored and prevents the system from finding the same dead end again).

Is the block a master or slave: There are some tasks that must be done before others, and some that should be done after others. Example: each batch will require DAB to be added to the slides at some particular point. Whoever, our instrument has on-board DAB mixing. Thus, the step of mixing the DAB on-board in a mixing vessel must be undertaken before the first batch requires DAB applied. In such a case the block of preparing DAB is a master block compared to a normal block. A slave lock is where a block must occur after another block. An example is where the DAB mixing vial is cleaned after a run. DAB mixing block can be cleaned at any time after the last DAB is applied to the last batch.

A description of mixing can be found in A METHOD AND APPARATUS FOR FLUID DISPENSATION, PREPARATION AND DILUTION, Australian Patent Provisional patent application No. 2003901871, the contents of which are hereby incorporated by reference.

Also incorporated by reference is Australian Provisional Patent application 2003900780 by the same applicant and its subsequent PCT application (number not yet allocated).

A method of generating a schedule will be described below.

The method assumes some blocks in the schedule have been selected but that the schedule has not been run on the apparatus. As such, the block chosen is block 5 in a sequence. Other cases will be discussed below as well.

Step 1:
Generate a pool of blocks from the list of available blocks (If there are 3 batches, then there will be a first block of each batch ready for scheduling).
Example Batch 1 block 5 (B1.5), Batch 2 block 5 (B2.5) and Batch 3 block 5 (B3.5)

Step 2:
Choose randomly from the pool (eg assume B1.5 is selected)

Step 3:
Position selected batch (B1.5) earliest in time. That is, place it straight after the last block scheduled for that batch (B1.4).

Step 4: check if the placement of selected block (B.1.5) causes a conflict between that batch and another previously scheduled block. This is done by comparing the use times of block B1.5 with the use time of the last scheduled block in one of the other batches, if no use time conflict arises, the use time of the other block is compared, and if not conflict arises, the block 1.5 is scheduled. If a conflict arises from If not, then block b1.5 is scheduled.

If conflict arises, move block b1.5 to a next available position where conflict does not arise (ie delay block).

Step 5: Check delay to see if it exceeds allowable open time for block. If not, then block B1.5 scheduled, and start process over.

If open time violation occurs, put block B1.5 back into pool.

Unschedule block scheduled immediately before Block 1.5. This may be for example block 1.4 or may be block 2.4 or block 3.4 for example. If the previously scheduled block is not from the same batch (i.e. not block 1.4), then the previously scheduled block is unscheduled and block 1.5 is scheduled in its place. The previously scheduled block (eg block 2.4 or block 3.5) goes back into the pool, from which a random selection is made. Of course new open time violations may be encountered and this algorithm is designed to search the tree of possible solutions for the schedule by moving back up the tree, then moving randomly down another branch. In this respect, other known algorithms that search trees for solutions may be employed.

If the block is from the same batch (i.e. block 1.4) then it is unscheduled and the block before it is unscheduled as well. Each block before is unscheduled until a block not of the same batch is encountered.

This routine may need to be run many times to produce a pool of schedules, wherein the best schedule is selected from the pool for use on the slides.

The random selection of blocks from a pool allows the scheduler to produce schedules that have a better chance of finding a suitable, if not optimal solution. Generally a time limit is set to stop the schedule generation, because in some circumstances it may take a very long time to calculate all possible combinations. In fact the pool of combinations may be infinite. Other method of limiting scheduling may be to stop after a set number of schedules are obtained, or to put a minimum time on the schedules time located. That is, stop scheduling if a schedule is found that takes less than a predetermined time.

It should be noted that a master block will always be scheduled before another equivalent block, and a slave batch will always be scheduled after an equivalent block, as these blocks are not part of the pool from which random blocks are chosen.

In the above example, the scheduler was run when a previously scheduled batch existed but had not been implemented by the apparatus. If the scheduler is run with no previous batches scheduled, eg three fresh batches are loaded into the apparatus, then the first block can be easily scheduled as it cannot conflict with other blocks. If the second block cannot be scheduled then a new first block is chosen, and so on. There may be times when the batches cannot be scheduled together, and in this case a batch may be unloaded from an instrument and stored while the remaining batches are scheduled and run. It may be possible to find a successful schedule by loading the third batch during the run of the other two batches as the scheduler will have a different start point and therefore may successfully find an acceptable schedule.

Insertion of Hydration Steps

When a schedule cannot be generated, it is possible to extend the starting time of a new batch by inserting steps to hydrate the slides in the batch. The hydration step will be of short duration, and should be fairly easy to schedule in. Since it will have an open time, it does not have to be performed immediately. This will allow the first block in the new batch to be delayed by as much as the sum of the hydration step's open time and use time. It is also possible to insert more than one hydration step.

It may be possible to insert hydration steps in between any two blocks in a batch, but it is believed that the complexities of the chemistries require that the hydration steps be inserted at the start only. Otherwise, each block could have unique rules for how many hydration steps could be inserted, and what their open times would be. This would increase the complexity both of the scheduler, and of validating the instrument's chemistries.

To provide a degree of certainty in determining an appropriate schedule the use and free times of each block are of a predetermined, fixed duration, as compared to the known methodology where the duration of various operational steps is varied, as needed. To further simplify matters, various reagents applied to the samples can be modified such as by altering the relevant reagent concentrations, so that at least some of the incubation operations are of the same duration. The system may also allow for some changes to be input by an operator to alter, for example, a primary antibody, the incubation times or slide temperature, prior to scheduling.

In the present example the reagents to be applied to the slides have been adapted to allow different tests to have similar or compatible protocols. For example, each different primary antibody is able to be applied to the sample on the slide for the same amount of time. This allows sequential application of the reagent to the slides one after the other on a tray (batch). For example, a dispense operation will deposit reagent such as primary antibody on each slide in a tray sequentially, and wash off the reagent after the time determined by the protocol sequentially as well. This provides a set incubation time for all slides in a tray or batch. An example is where a protocol defines that a buffer be applied to the slides in a batch, then a primary antibody, followed by an incubation time and a wash. A triplet is formed from starting from an open time allowed after the application of buffer to the slides. That is, primary antibody may be applied to the slides in a batch immediately after exposure of the slides to buffer solution, or delayed by a predetermined time. This possible delay is called an open time, and a triplet always starts with an open time. In the case of buffer exposure the open time is non-zero. After exposure of a buffer, the application of primary antibody is a use time, as it requires use of a critical resource, being the robot arm and nozzle 11. An incubation time then follows, which is a free time. Thus a triplet may be a open time (buffer exposure) a use time (reagent application) and a free time (incubation, where no resources are used). The protocols for all batches are sent to the scheduler, which constructs blocks from the triplets. The rules for block contruction are that a block begins and ends with a non-zero open time. Thus several triplets can be merged into a block where the triplets within the block (ie not first triplet) have a zero open time. The block ends when the next triplet in the batch has a non-zero open time. From the construction of the blocks within each batch, a schedule between bathces can be constructed as the scheduler has assembled fixed blocks of use and free time separated by known open time.

The following are definitions of terminology used herein:

Critical resource: a resource that that can only do a single operation at once, and can thereby only perform one step at a time. Critical resources predominantly refer to the robot arm of the system, but can include other systems that may only be used on a single batch at once.

Use time: the length of time for which a resource (such as a critical resource) is being used by a protocol, and therefore not available for use by other protocols.

Free time: The length of time when an action does not use critical resources. This can be within or between blocks.

Open time: time when a block does not require a critical resource, starting after the conclusion of the previous block in the same batch. The length of an open time is not predefined, and depends on a schedule. Open time can be zero or up to a time controlled by parameters relating to tissue sample type and apparatus configuration.

Batch: a sequence of blocks required to implement the protocols in a tray or other grouping of slides. Typically this is physically embodied by a group of test samples located in a single tray.

Open time violation: when the scheduled time between blocks that is in excess of the allowable open time.

Use time conflict: When two or more batches are scheduled to have overlapping use times for the same critical resource.

The invention claimed is:

1. A method of processing a plurality of biological samples in an apparatus, comprising:
scheduling delivery of a reagent to a plurality of sample slides arranged in batches, via a robotic arm of the apparatus, according to a sequence of steps in a protocol, including:
establishing, using a controller executed on a computer, a plurality of protocols for the batches, respectively, with each protocol having at least one block of dispensing and incubation operations, defining use and free times, respectively; and
creating a schedule that contains interleaved blocks from each of the protocols by time shifting the blocks such that use time violations between the blocks are avoided,
wherein the use time is a time when the robotic arm is in use by a step of a given protocol from among the plurality of protocols, and the free time is a time where duration of the step of the given protocol has not completed but the robotic arm is not in use by the given protocol, and use time violations occur where the robotic arm is required to be in use by two protocols from among the plurality of protocols at the same time,
wherein the creating further comprises creating the schedule that contains interleaved blocks from each of the protocols by time shifting the blocks such that open time violations between the blocks are avoided, wherein an open time violation occurs when a gap between two blocks within the same protocol exceeds a predetermined maximum time indicated by a subsequent block among the two blocks.

2. A method as claimed in claim 1, wherein the method includes establishing a new schedule to accommodate one or more batches, added after commencement of operations of an initial scheduling.

3. A method as claimed in claim 2, wherein if a new schedule cannot be generated, to accommodate a batch added after commencement of operations of an initial scheduling, one or more hydration steps are included to extend a start time of the added batch.

4. A method as claimed in claim 1, wherein at least two protocols are established for each batch.

5. An apparatus for processing a plurality of biological samples comprising:
- a plurality of reagent containers;
- a plurality of independently accessible sample slides arranged in batches;
- a robotic arm;
- a reagent transfer device for transferring reagents from the reagent containers to the sample slides;
- an identifier scanner;
- a controller for operating the apparatus,
- wherein the controller schedules reagent delivery to a plurality of sample slides arranged in batches, wherein the schedule includes: establishing a protocol for each of the batches, with each protocol having at least one block of dispensing and incubation operations, defining use and free times, respectively and
- wherein the controller creates the schedule by interleaving blocks from each of the protocols by time shifting the blocks such that use time violations between the blocks are avoided,
- wherein the use time is a time when the robotic arm is in use by a step of a given protocol from among the plurality of protocols, and the free time is a time where duration of the step of the given protocol has not completed but the robotic arm is not in use by the given protocol, and use time violations occur where the robotic arm is required to be in use by two protocols from among the plurality of protocols at the same time,
- wherein the controller creates the schedule that contains the interleaved blocks from each of the protocols by time shifting the blocks such that open time violations between the blocks are avoided, wherein an open time violation occurs when a gap between two blocks within the same protocol exceeds a predetermined maximum time indicated by a subsequent block among the two blocks.

* * * * *